United States Patent
Kluge (10) Patent No.: US 9,427,561 B2
(45) Date of Patent: Aug. 30, 2016

(54) METHOD FOR OPERATING IN A SYSTEM FOR REPETITIVE LOCAL PUNCTURING OF SKIN AND SYSTEM

(71) Applicant: MT. DERM GmbH, Berlin (DE)

(72) Inventor: Joern Kluge, Teltow (DE)

(73) Assignee: MT.DERM GMBH, Berlin (DE)

( * ) Notice: Subject to any disclaimer, the term of this patent is extended or adjusted under 35 U.S.C. 154(b) by 177 days.

(21) Appl. No.: 14/109,261

(22) Filed: Dec. 17, 2013

(65) Prior Publication Data

US 2015/0164543 A1 Jun. 18, 2015

(51) Int. Cl.
*A61B 17/34* (2006.01)
*A61M 37/00* (2006.01)

(52) U.S. Cl.
CPC .. *A61M 37/0076* (2013.01); *A61M 2037/0023* (2013.01); *A61M 2210/0606* (2013.01)

(58) Field of Classification Search
CPC ...... A61B 17/34; A61B 17/50; A61B 19/00; A61M 37/0076; A61M 37/00; A61M 37/0084
See application file for complete search history.

(56) References Cited

U.S. PATENT DOCUMENTS

| | | |
|---|---|---|
| 2005/0010236 A1 | 1/2005 | Frister |
| 2006/0020283 A1 | 1/2006 | Lisec |
| 2008/0033356 A1 | 2/2008 | Kluge et al. |
| 2008/0033470 A1 | 2/2008 | Kluge et al. |
| 2008/0077170 A1 | 3/2008 | Kluge et al. |
| 2010/0036317 A1 | 2/2010 | Oginski et al. |
| 2010/0192730 A1 | 8/2010 | Dubin |
| 2012/0158032 A1 | 6/2012 | Jarling |
| 2012/0179189 A1* | 7/2012 | Zingaretti .......... A61B 19/2203 606/187 |
| 2013/0123825 A1 | 5/2013 | Demjanenko |

FOREIGN PATENT DOCUMENTS

WO 2013/076715 A1 5/2013

* cited by examiner

*Primary Examiner* — Victor Nguyen
(74) *Attorney, Agent, or Firm* — Leason Ellis LLP (57) ABSTRACT

A method for operating a system for repetitive local puncturing of skin is provided. The system having a handheld applicator device provided with a puncturing device configured to repetitively puncture skin and a control device connected to the handheld applicator device and configured to control operation of the applicator device. The method includes receiving a user selection for a body skin part to which repetitive local puncturing is to be applied in the control device, responsively providing a set of operation parameters in the control device, the set of operation parameters defining a mode of operation of the applicator device for repetitive local puncturing, and operating the applicator device according to the mode of operation defined by the set of operation parameters with the operating of the applicator device being controlled by the control device. Also, a system for repetitive local puncturing a skin is provided.

15 Claims, 4 Drawing Sheets

METHOD FOR OPERATING IN A SYSTEM FOR REPETITIVE LOCAL PUNCTURING OF SKIN AND SYSTEM

The present disclosure refers to a method for operating in a system for repetitive local puncturing of a skin and a system.

BACKGROUND

Such systems for repetitive local puncturing a skin are usually provided with a control device and an applicator device functionally connected to the control device. Intern the applicator device may be provided with a driving unit and a puncturing unit driven by a driving force provided by the driving unit.

The system for repetitive local puncturing the skin may be used, for example, for tattooing and applying permanent make-up. Also, the system may be used for locally puncturing the skin without applying a colorant to the skin. With respect to other examples, the system may be used for applying a cosmetic or medical substance to a patient's skin.

Also, microneedling may be applied to the skin. The term microneedling as used here refers to applying local puncturing the skin over an application area of the skin with or without additionally applying a cosmetic or medical substance. Such microneedling may be used for skin regeneration. Microneedling is a concept that can make the skin look younger by reducing lines, scars and discoloration. Applying tiny micro-punctures to the skin with fine needles may stimulate the body's natural healing response, promoting the proliferation of skin cells and/or the production of collagen.

A system for repetitive local puncturing a skin, for example, is disclosed in US 2010/0192730 A1. A control device for a tattoo machine and a tattoo system are described. The control device is adapted to control reciprocation of a needle assembly of the tattoo machine using a pulsed signal. A duty circle of the pulsed signal is controlling a stroke length of the needle assembly. A frequency of the pulse signal is controlling a stroke frequency of the needle assembly. Duty circle and frequency may be controlled independently of one another.

Further systems are disclosed in US 2008/0033470 A1 and US 2008/0033356 A1.

SUMMARY OF THE INVENTION

It is an object of the present disclosure to provide improved technologies for a system for repetitive local puncturing of skin, especially in relation to adjusting a mode of operation in the system.

A method for operating a system for repetitive local puncturing of a skin is provided according to claim 1. Further, a system for repetitive local puncturing of a skin is provided according to claim 17. Further developments are disclosed in the independent claims.

According to one aspect, a method for operating a system for repetitive local puncturing of a skin is provided. The system is having a handheld applicator device provided with a puncturing device which is configured to repetitively puncture a skin. Further, the system comprises a control device which is operatively connected to the handheld applicator device and configured to control operation of the applicator device. The method for operating the system for repetitive local puncturing the skin comprises receiving a user selection for a body skin part to which repetitive local puncturing is to be applied in the control device. The body skin part may refer to any part of a patient's skin. In response to receiving the user's selection, a set of operation parameters is provided in the control device. In a simple embodiment, the set of operation parameters may comprise only one operation parameter. The one or more operation parameters define a mode of operation for the applicator device for repetitive local puncturing for the body skin part. The set of operation parameters is assigned to or associated with the body skin part, i.e. the set of operation parameters define a mode of operation which is favorable to be used in the process of puncturing the body skin part selected by the user. Different sets of operation parameters for different body skin parts may be distinguished by one or more operation parameter. Following, the applicator device is operated according to the mode of operation defined by the set of operation parameters under the control of the control device.

According to another aspect, a system for repetitive local puncturing of a skin is provided. The system comprises a handheld applicator device provided with a puncturing device configured to repetitively puncture a skin, and a control device connected to the handheld applicator device and configured to control operation of the applicator device. The system is adapted to receive a user selection for a body skin part to which repetitive local puncturing is to be applied in the control device, in response to the user selection, provide a set of operation parameters in the control device, the set of operation parameters defining a mode of operation of the applicator device for repetitive local puncturing for the body skin part, and operate the applicator device according to the mode of operation defined by the set of operation parameters, the operating of the applicator device being controlled by the control device.

The receiving the user selection may comprise receiving a user selection for a face part. In this case the user's selection is received for mode of operation used for local puncturing an area of the patient's face. For example, a set of operation parameters for applying permanent make-up or microneedling to the patient's face may be provided.

The receiving the user selection may comprise detecting a user selection of a control element of the control device. The control element may be provided by at least one of a touch sensitive screen, one or more switches provided on the control device, and a mouse connected to the control device.

The method may further comprise displaying a representation of one or more body skin parts on a display connected to the control device. The display may be provided by a display element which is part of the control device (internal display). As an alternative or in addition, an external display device connected to the control device may be provided.

The step of receiving the user selection may comprise receiving a user input indicating one or more application parameters in the control device. The one or more application parameters, in addition to the body skin part selection by the user, further define one or more characteristics of the local puncturing of the skin. For example, an application parameter may refer to at least one of user identification, patient's identification, patient's age, gender and skin characteristics. In addition or as an alternative, one or more application parameters may be provided as measured parameters collected by one or more measuring devices and automatically integrated into the set of application parameters.

The step of providing the set of operation parameters may comprise amending the set of operation parameters in response to the user input indicating one or more application parameters. Thereby, the user is allowed to amend one or more operation parameters originally contained in the set provided by the control device in response to the user's selection of the body skin part.

The providing of the set of operation parameters may comprise a step of selecting a set of operation parameters defining a mode of operation of the applicator device for repetitive local puncturing, the set of operation parameters being assigned to the body skin part and the one or more application parameters. In this case, in response to the user selection and the user input, the set of operation parameters may automatically be selected by the data processing device of the control device, the set of operation parameters being assigned to or associated with both the selected body skin part and the one or more application parameters.

The one or more application parameters may be selected from the group of the following application parameters: patient's age, patient's gender, skin thickness, skin elasticity, skin type, fat content of skin, skin wrinkle distribution, and skin wrinkle depth.

The set of operation parameters may comprise one or more operation parameters selected from the following group: needle stroke length, needle stroke repetition frequency, applied puncturing force, and needle front projection. The parameters referring to the element "needle" may refer to a single needle or a group of needles. Also, a needle plate may be provided, such needle plate being known as such for a system for repetitive local puncturing of a skin.

The providing the set of operation parameters may comprise outputting a needle module recommendation to the user, the needle module recommendation indicating a type of needle module which is connectable to a driving module of the applicator device and which comprises a puncturing device.

In an embodiment, the method may comprise receiving user control input, and amending the set of operation parameters to a set of amended operation parameters in response to the user control input. In first place, an original set of operation parameters may be provided in the control device in response to the user selection of the body skin part. The original set of operation parameters may be amended by the user, thereby providing an amended set of operation parameters. The set of amended operation is representing an amended mode of operation. Following, the applicator device may be operated according to the amended mode of operation defined by the set of amended operation parameters. The amended set of operation parameters may be generated prior to running the applicator device under the control of the control device, or during a running control session in which the applicator device is operated according to the original set of operation parameters.

The method may comprise storing operation data in a memory device, the operation data comprising electronic information about at least one of the set of operation parameters and the set of amended operation parameters. The memory device may be part of or connected to the control device. The memory device may be provided in a data base implemented separately from the control device, for example, in a network system to which the control device may connect. The operation data and/or the amended operation data may be stored for a person, e.g. the patient and/or the user of the device, thereby, the operation data being assigned to or associated with the person were used, e.g. the patient for which the set of operation parameters and the set of amended operation parameters, respectively, and/or the user operating the system for repetitive local puncturing of the patient's skin. Such electronic data referring to the operation and assigned to the person may be stored for each skin area to which local puncturing was applied. Separate data for different body skin areas or parts may be stored. The person may be identified by a personal identification, e.g. name and/or some alphanumeric code, received in response to a user input in the control device or automatically assigned by the control device.

The method may further comprise receiving a new user selection for the body skin part for a later treatment in the control device, and providing the set of amended operation parameters as a pre-selection of operation parameters in the control device for a later operation of the applicator device. The amended operation parameters used for the former treatment of the same body skin part and provided as a pre-selection may be amended by the user in response to the new user selection for the body skin part for the later treatment.

The method may further comprise determining a mean value for at least one of the operation parameters. The determination of the mean value may be provided in response to receiving a plurality of user control inputs for the at least one the operation parameters. In different operations of the control device, the operation parameter may be applied as proposed in the original set of operation parameters or according to the amendment caused by the user definition received. Different mean values may independently be determined for different body skin parts, so that a different mean value may exist for each body skin part.

In another example, the method may further comprise determining a deviation value or factor for at least one of the amended operation parameters, and applying the deviation value to another operation parameter. The other operation parameter may be an operation parameter from the same set of operations parameters, but different from the one for which the deviation was determined. As an alternative, the other operation parameter may be an operation parameter from a different set of operation parameters, e.g. a set of operation parameters used in or proposed for a later treatment of the same or a different body skin part. The deviation value or parameter of change may be an absolute or a relative (percent) value. There may be a plurality of deviation factors (set of deviation factors) each of the deviation factors relating to a different operation parameter. The one or more deviation factors may be electronically stored as personalized or individualized deviation factors assigned to a user, e.g. a physician. In a later treatment for local puncturing the user may identify himself to the control device. In response to the identification the control device may provide the operation parameters to which the individualized deviation factor(s) are applied already.

One or more factors and/or a functional term may be applied to the deviation factor determined as such. For example, the deviation factor derived from the difference between a proposed operation parameter and a user defined operation parameter may be multiplied by a fixed term or factor.

A mean value may be determined for a deviation value. For example, with respect to a selected body skin part a plurality of different deviation values may be determined in the control device. The plurality of deviation values may be due to treatment of a group of patients by one and the same user. Determining a mean value for the plurality of deviation factors will provide for a personal or individualized mean deviation value for such user, e.g. a physician. Next time a set of operation parameters is generated in the control device, the personal mean deviation value may be applied automatically for providing an individualized set of operation parameters.

The method may further comprise:
receiving a further user selection for a further body skin part to which further repetitive local puncturing is to be applied in the control device, the further body skin part being different from the body skin part,
in response to the further user selection, providing a set of further operation parameters in the control device, the further operation parameters being different from the operation parameters and defining a further mode of operation of the applicator device for the further repetitive local puncturing of the further body skin part, and
operating the applicator device according to the further mode of operation, the operating of the applicator device being controlled by the control device.

In this embodiment, different modes of operation are used with the same system.

BRIEF DESCRIPTION OF THE DRAWINGS

In the following, further embodiments are described with reference to Figures. In the Figures show.

DETAILED DESCRIPTION OF THE PREFERRED EMBODIMENTS OF THE INVENTION

Figure 1:
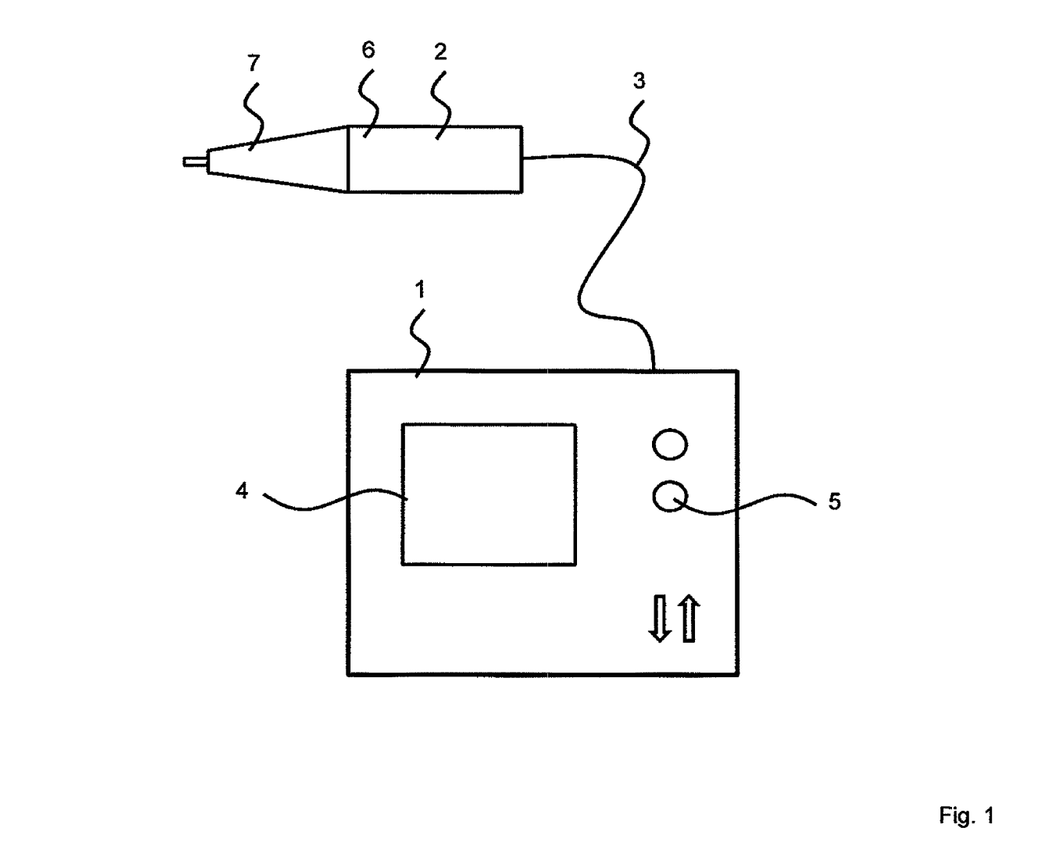
FIG. 1 a schematic representation of a system for repetitive local puncturing of skin, and FIG. 2 a schematic representation of a display area displaying a human face, FIG. 3 a schematic representation of a method for operating or controlling in a system for repetitive local puncturing skin, and FIG. 4 a schematic representation of another example of operation of the system for repetitive local puncturing.

FIG. 1 shows a schematic representation of a system for repetitive local puncturing of skin. The system may be used for locally puncturing the skin of a human being or an animal. The system comprises a control device 1 and a handheld applicator device 2. In the embodiment shown in FIG. 1, the control device 1 and the handheld applicator device 2 are connected by a cable 3. As an alternative, there may be a cable free or wireless connection between the control device and 1 and the handheld applicator device 2. For example, bluetooth technology may be used for exchanging electronic signals between the control device 1 and the handheld applicator device 2. Also, the control unit 1 may be directly connected, e.g. mechanically, to or integrated into the handheld applicator device 2.

In general, the control device 1 provides control signals for operating the applicator device 2 which is hold by hand by the user during the skin puncturing which may be applied, for example, for tattooing, applying permanent make-up or microneedling. The handheld applicator device 2 is provided with a puncturing device comprising, for example, a needle assembly. The needle assembly is repetitively moved forward and back for repetitive local puncturing the skin.

Different embodiments of handheld applicator devices are known as such. In this respect, reference is made to the following documents: US 2005/0010236 A1, US 2006/0020283 A1, US 2008/0077170 A1, US 2010/0036317 A1, US 2012/0158032 A1 and US 2013/0123825 A1.

Also, a roller provided with a group of needles in the roller surface may be used. The roller may be driven by a motor device for which operation parameters are provided by the control device 1. Such a device as such is disclosed in WO2013/076715.

As can be seen in FIG. 1, the control device 1 is provided with a display area 4 on which a menu for user selection may be displayed. The display area 4 may be provided by a touch sensitive display and/or may be responsive to an input device 5 comprising a plurality of input elements and connected to or provided on the control device 1. The menu to be displayed in the display area 4 provides the option for selecting the body skin part, for example, an area of the face of the patient or some other skin area of the patient's body, to which the local puncturing shall be applied.

Figure 2:
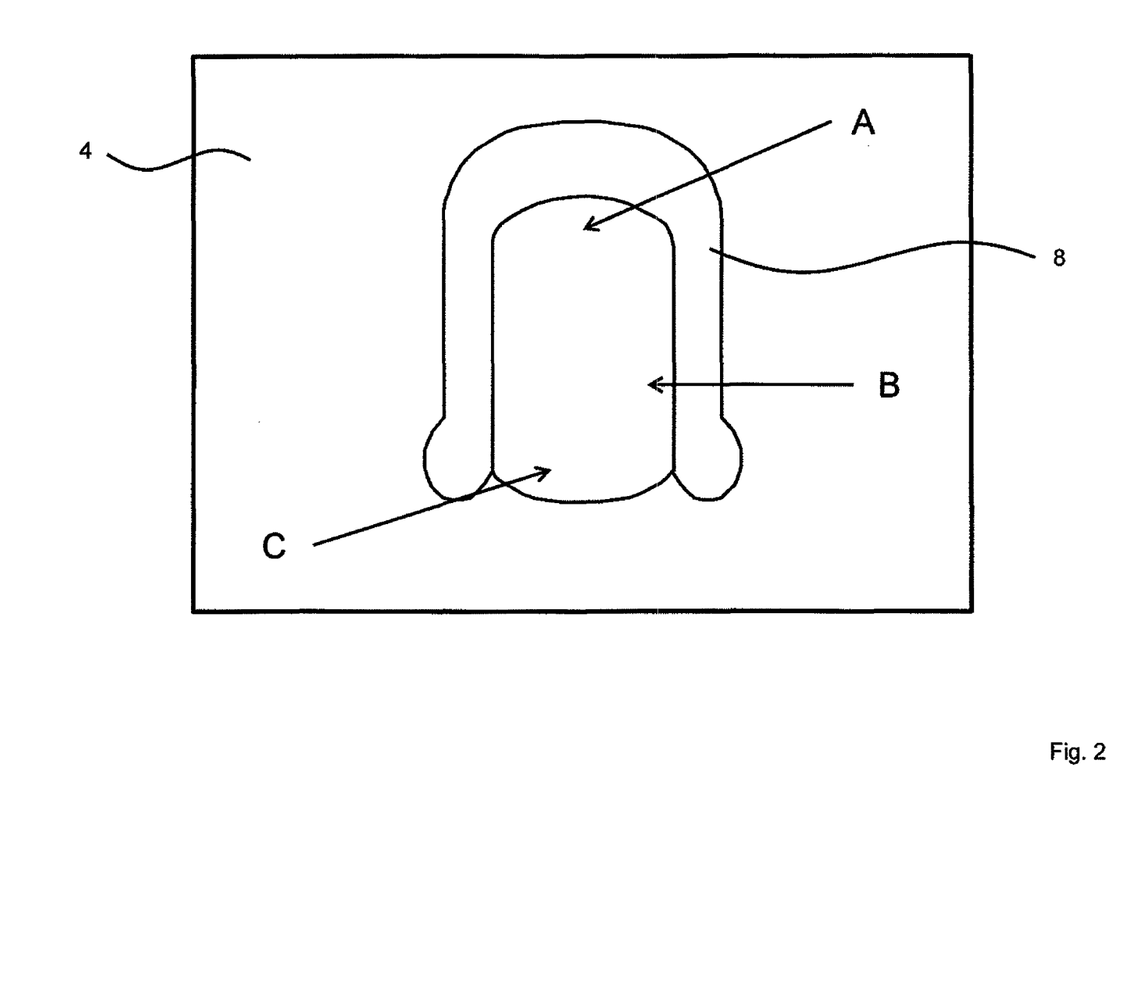

For example, a schematic representation of a human face 8 may be presented in the display area 4 (see FIG. 2). The user of the system for repetitive local puncturing may select a certain part of the face displayed. According to the embodiment shown in FIG. 2, face parts A, B, and C may be selected by the user for local skin puncturing.

A data processing device provided in the control device 1, in response to receiving the user selection, will provide a set of operation parameters in the control device 1. The set of operation parameters may comprise one or more operation parameters selected from the following group: needle stroke length, needle stroke repetition frequency, applied puncturing force, and needle front projection. The needle front projection defines at which extent the one or more needles of the puncturing device are projecting from the tip of the handheld applicator device 2 at least in the extended position.

After providing the set of operation parameters which in turn define a mode of operation of the handheld applicator device 2, further user input may be received in the control device 1 for confirming or amending the set of operation parameters. After the original or an amended set of operation parameters is confirmed by the user, the handheld applicator device 2 may be operated according to the set of operation parameters under the control of the control device 1.

In the course of using the system the user may select a different body skin part, for example, a different area of the patient's face, after a first application, for which the set of operation parameters confirmed by the user was applied, is finished.

The set of operation parameters confirmed by the user may be stored in a memory device of the control device 1. The electronic information referring to the stored set of operation parameters may be assigned to or associated with the user and/or the patient, e.g. by storing additional electronic information indicating that the set of operation parameters stored belongs to the patient. Therefore, the set of operation parameters used before may be retrieved for a later session for locally puncturing the skin of the same patient.

Together with or separated from the set of operation parameters provided in response to the user's selection, a needle module recommendation may be provided to the user by the control device 1. In case of different needle module configurations which differ, for example, with respect to the type and/or thickness of the needles, in response to the user selection a certain needle module may be recommended to the user due to the user selection of a certain body skin part. If a selected needle module was used for local puncturing of the patient's skin, electronic information about the selected needle module may also be stored in the memory device of the control device 1. Referring to FIG. 1, the handheld applicator device 1 comprises a driving module 6 and a needle module 7 connected to the driving module 6. By the driving module 6 a driving force for reciprocation of the one or more needles received in the needle module 7 is provided. To the driving module 6 different needle modules may be coupled depending on the application case. In one embodiment, the different needle modules may differ with respect to the type of needle assembly. The assembly may be provided with one needle, a group needles or a needle plate.

By the data processing device of the control device 1 electronic information about one or more sets of operation parameters used for one and the same body skin part may be processed. From such information the data processing device may determine a set of mean operation parameters. The set of mean operation parameters may be provided as a starting set of operation parameters in a response to the user's selection of a certain body skin part.

A mean value for user-defined operation parameter change may be determined after receiving user input for amending original operation parameters provided by the control device 1 several times. Again, electronic information for such mean value which may apply to one or more skin areas may be assigned to or associated with the patient and/or the user. A mean value may be determined in relation to different operation parameters and/or different procedures. For example, a mean value of an operation parameter may be determined for several treatments of the same body skin part, such mean value being determined for only one patient or a group of patients. On the other hand, a mean value could be determined for an operation parameter, e.g. front needle projection, used for treatments of different body skin parts.

After some amendment of operation parameter(s) to further operation parameter(s), the further operation parameter(s) may be compared to the operation parameter(s). One or more deviation factors (parameter of change) may be calculated. Upon selection of a different skin part the deviation factor may be taken into account for the calculation of the operation parameters. If, for example, the skin on the forehead is treated with a higher needle front projection compared to the original suggested operation parameter, then the other skin areas should also be treated with a higher needle front projection. The higher needle front projection in absolute or relative values may be the same for all skin area parts. As an alternative, the higher front projection may be different for different skin areas of the same patient, but it may be the same in relative values compared to the original values. For example, for a patient a front needle projection may be applied which for all skin area part is higher by 20% compared to the front needle projection proposed by the control device 1 originally after receiving a first user selection.

The parameter of change may also be determined by comparing one or more mean operation parameters may also be used to determine further operation parameters.

The step of receiving the user selection for the body skin part to which repetitive local puncturing shall be applied may comprise receiving a user input indicating one or more application parameters in the control device 1. The application parameters may comprise one or more parameters selected from the following group: patient's age, patient's gender, skin thickness, skin elasticity, skin type, fate content of skin, skin fold distribution, and skin fold depth. One or more operation parameter may be used as an additional criterion in the process of providing the set of operation parameters in response to the user selection for the body skin part to which repetitive local puncturing is to be applied in the control device 1.

One of the application parameters may also be the number of treatment the patient has received. It can be an advantage to set different application or operation parameters for different treatments.

Figure 3:
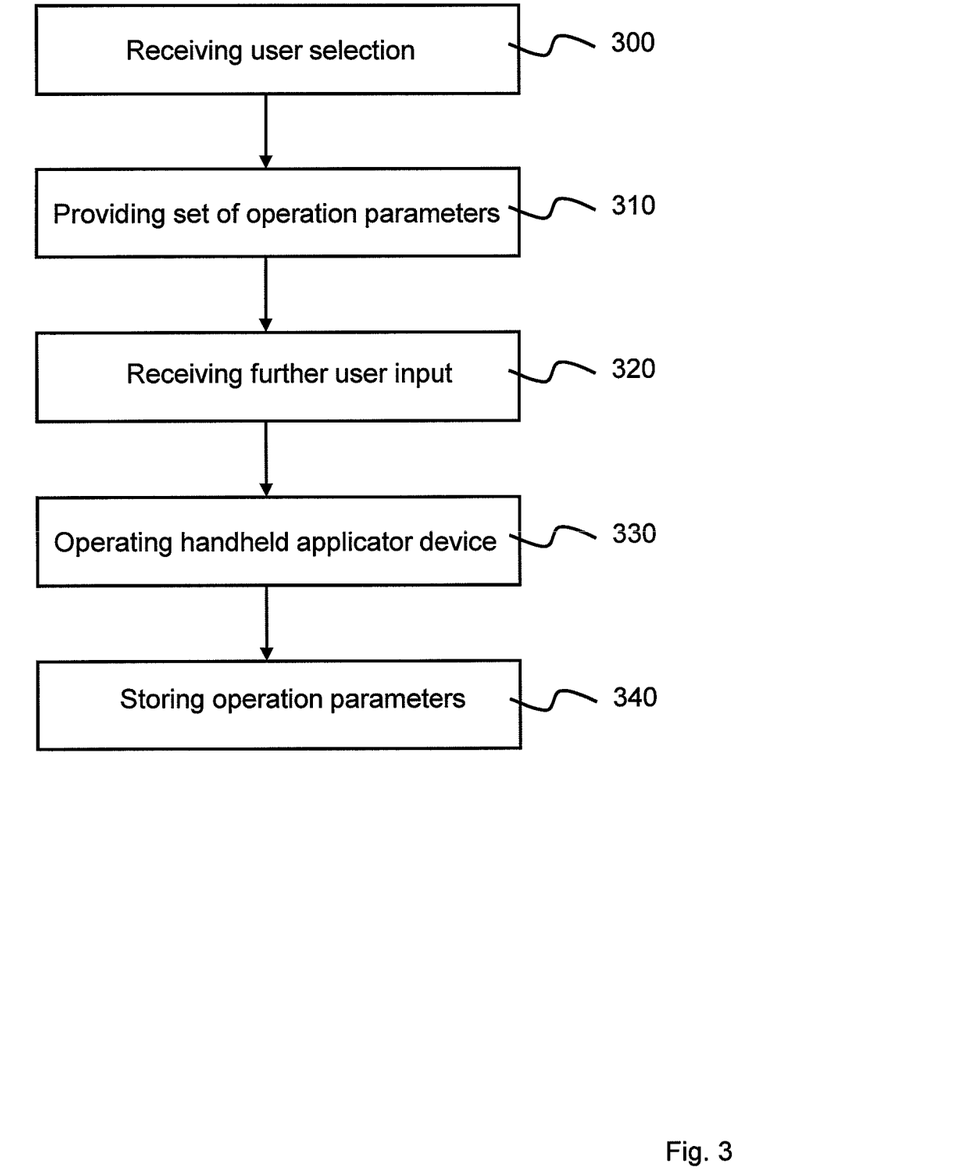

Referring to FIG. 3, a further example of a method for operating in a system for repetitive local puncturing skin is described. In a step 300, the user selection for a body skin part to which repetitive local puncturing is to be applied is received in the control device 1. In response to the user selection, a set of operation parameters is provided in the control device 1 in step 310. The set of operation parameters defines a mode of operation of the applicator device 2 for repetitive local puncturing for the body skin part selected by the user. According to the example depicted in FIG. 3, in step 320 a further user input for amending one or more of the parameters of the set of operation parameters provided in response to the user selection is received in the control device 1. For example, the user may amend a repetition frequency and/or the penetration depth individually compared to the set of operation parameters provided in response to the user selection. Following, in step 330 the handheld applicator device 2 is operated according to the operation parameter(s) amended by the user and the remaining operation parameters of the set of operation parameters not amended.

In step 340, the parameters used for the operation of the handheld applicator device 2 are stored in a memory device. Thereby, the operation parameters actually used for locally puncturing a selected skin area are made available for later use for operating the handheld applicator device 2 for the same or some other patient. As an option, the stored operation parameters may be assigned to the patient. For example, together with the electronic data representing the used operation parameters patient identification information may be stored. In a possible example, the name or an identification number may be stored.

Figure 4:
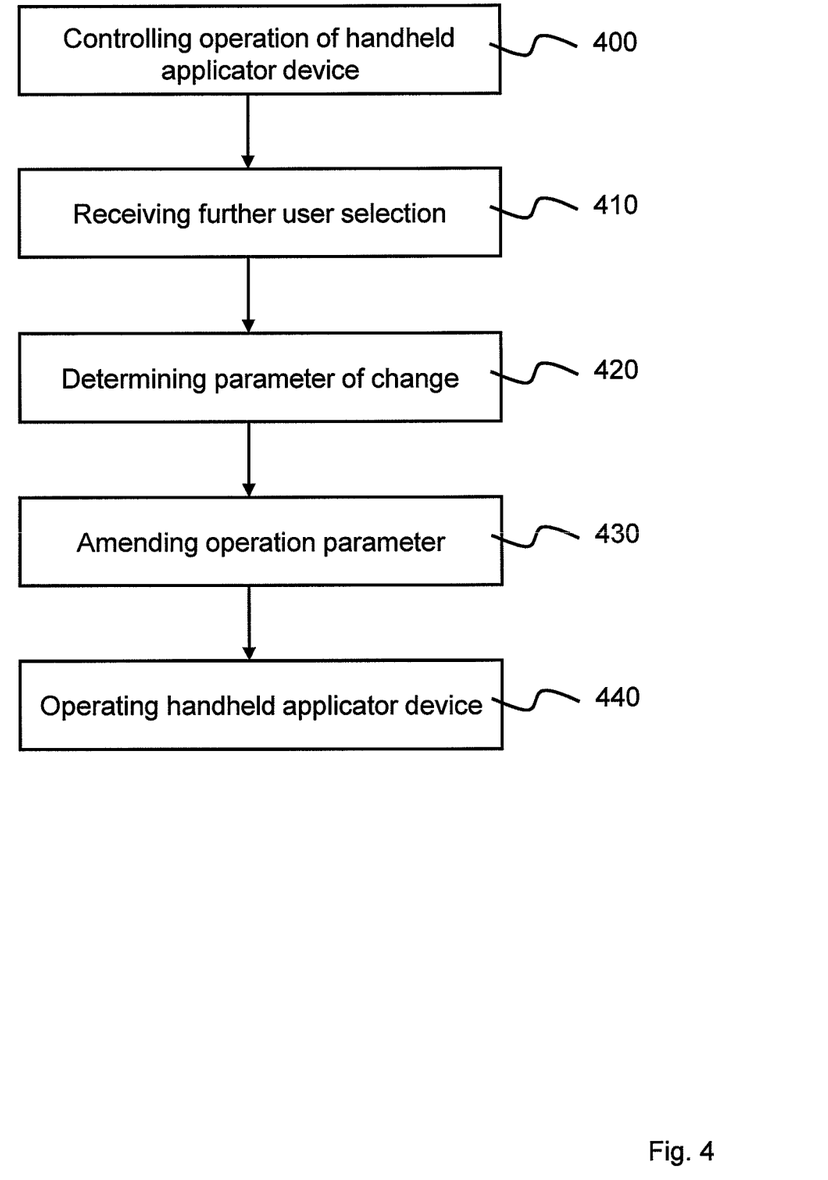

FIG. 4 shows a schematic representation of another example of operation of the system for repetitive local puncturing of a skin which optionally may be combined with other methods described. In a step 400, the handheld applicator device 2 is operated or controlled according to a set of operation parameters which contain at least one amended operation parameter amended according to a received user input. In step 410, in the control device 1 a further user selection for a body skin part to which repetitive local puncturing is to be applied is received. Such user selection is received after local puncturing operation was done for a different skin part before.

In the next step 420, a parameter of change is determined from a comparison of the at least one amended operation parameter and the original operation parameters provided with the set of original operation parameters and amended according to the user input received. For example, the parameter of change may indicate an amendment of about 10% compared to the original operation parameter which was automatically provided by the control device 1. Such step for determining the parameter of change or deviation factor/value may be performed prior or in response to receiving further user selection. It may be performed whenever an operation parameter is amended according to a user input.

After the user selection for the different skin area was received in the control device 1, in step 430 the operation parameter, for example the puncturing frequency, provided in the set of operation parameters for the selected different skin area is automatically amended according to the parameter of change (deviation value/factor) determined before.

For example, the frequency defined in the original set of operation parameters is decreased or increased by 10%. One or more factors and/or a functional term may be applied to the deviation factor determined as such. For example, the deviation factor derived from the difference between a proposed operation parameter and a user defined operation parameter may be multiplied by a fixed term or factor. By the factor or term applied the deviation factor originally determined may be increase or decreased.

Following, in step 440 the handheld applicator device 2 is operated according to the operation parameter(s) amended automatically based on the parameter of change and/or by the user and the remaining operation parameters of the set of operation parameters not amended.

Electronic information about the parameter of change determined may be stored in the memory device. Such parameter of change may be assigned to or associated with the patient for whom the set of operation parameters was used. Such operation data assigned to the patient may be stored for each skin area to which local puncturing was applied. Separate data for different skin areas may be stored.

The features disclosed in this specification, the figures and/or the claims may be material for the realization of the disclosure in its various embodiments, taken in isolation or in various combinations thereof.

The invention claimed is:

1. A method for operating in a system for repetitive local puncturing of a skin, the system having a handheld applicator device provided with a puncturing device configured to repetitively puncture the skin and a control device connected to the handheld applicator device and configured to control operation of the applicator device, the method comprising:
   receiving a user selection for a body skin part to which repetitive local puncturing is to be applied in the control device,
   in response to the user selection, providing a set of operation parameters in the control device, the set of operation parameters defining a mode of operation of the applicator device for repetitive local puncturing for the body skin part,
   operating the applicator device according to the mode of operation defined by the set of operation parameters, the operating of the applicator device being controlled by the control device,
   receiving user control input,
   amending the set of operation parameters to a set of amended operation parameters in response to the user control input, and
   storing operation data in a memory device, the operation data comprising electronic information about at least the set of amended operation parameters.

2. The method according to claim 1, wherein the receiving the user selection comprises receiving a user selection for a face part.

3. The method according to claim 1, wherein the receiving the user selection comprises receiving a user input indicating one or more application parameters in the control device.

4. The method according to claim 3, wherein the providing the set of operation parameters comprises amending the set of operation parameters in response to the user input indicating one or more application parameters.

5. The method according to claim 3, wherein the providing the set of operation parameters comprises selecting a set of operation parameters defining a mode of operation of the applicator device for repetitive local puncturing, the set of operation parameters being assigned to the body skin part and the one or more application parameters.

6. The method according to claim 3, wherein the one or more application parameters are selected from the group of the following application parameters: patient's age, patient's gender, skin thickness, skin elasticity, skin type, fate content of skin, skin fold distribution, and skin fold depth.

7. The method according to claim 1, wherein the set of operation parameters comprises one or more operation parameters selected from the following group: needle stroke length, needle stroke repetition frequency, applied puncturing force, and needle front projection.

8. The method according to claim 1, wherein the providing the set of operation parameters comprises outputting a needle module recommendation to the user, the needle module recommendation indicating a type of needle module which is connectable to a driving module of the applicator device and which is comprising the puncturing device.

9. The method according to claim 1, further comprising receiving a new user selection for the body skin part for a later treatment in the control device, and providing the set of amended operation parameters as a pre-selection of operation parameters in the control device for a later operation of the applicator device.

10. The method according to claim 1, further comprising determining a deviation value for at least one of the amended operation parameters, and applying the deviation value to another operation parameter.

11. The method according to claim 10, further comprising determining the deviation value as an individualized deviation value.

12. The method according to claim 1, further comprising determining a mean value for at least one of the operation parameters and I or the deviation value.

13. A method for operating in a system for repetitive local puncturing of a skin, the system having a handheld applicator device provided with a puncturing device configured to repetitively puncture the skin and a control device connected to the handheld applicator device and configured to control operation of the applicator device, the method comprising:
   receiving a user selection for a body skin part to which repetitive local puncturing is to be applied in the control device;
   in response to the user selection, providing a set of operation parameters in the control device, the set of operation parameters defining a mode of operation of the applicator device for repetitive local puncturing for the body skin part;
   operating the applicator device according to the mode of operation defined by the set of operation parameters, the operating of the applicator device being controlled by the control device;
   receiving user control input;
   amending the set of operation parameters to a set of amended operation parameters in response to the user control input;
   determining a deviation value for at least one of the amended operation parameters,
   applying the deviation value to another operation parameter; and
   automatically applying the deviation value to an operation parameter provided in response to receiving, in the control device, one of a user selection for repetitive local puncturing of a further body skin part being different from the body skin part and a user selection for later treatment of the body skin part.

14. The method according to claim 13, further comprising determining the deviation value as an individualized deviation value.

15. A method for operating in a system for repetitive local puncturing a skin, the system having a handheld applicator device provided with a puncturing device configured to repetitively puncture a skin and a control device connected to the handheld applicator device and configured to control operation of the applicator device, and the method comprising:

receiving a user selection for a body skin part to which repetitive local puncturing is to be applied in the control device;

in response to the user selection, providing a set of operation parameters in the control device, the set of operation parameters defining a mode of operation of the applicator device for repetitive local puncturing for the body skin part;

operating the applicator device according to the mode of operation defined by the set of operation parameters, the operating of the applicator device being controlled by the control device;

receiving a further user selection for a further body skin part to which further repetitive local puncturing is to be applied in the control device, the further body skin part being different from the body skin part;

in response to the further user selection, providing a set of further operation parameters in the control device, the further operation parameters being different from the operation parameters and defining a further mode of operation of the applicator device for the further repetitive local puncturing of the further body skin part; and operating the applicator device according to the further mode of operation, the operating of the applicator device being controlled by the control device.

\* \* \* \* \*